United States Patent [19]
Mazzola

[11] Patent Number: 5,948,671
[45] Date of Patent: Sep. 7, 1999

[54] CONTROL OF REPLANT DISEASE OF TREE FRUITS WITH *PSEUDOMONAS PUTIDA*

[75] Inventor: Mark Mazzola, Leavenworth, Wash.

[73] Assignee: The United States of America as represented by the Secretary of Agriculture, Washington, D.C.

[21] Appl. No.: 09/122,342

[22] Filed: Jul. 24, 1998

[51] Int. Cl.⁶ ............................... C12N 1/20; A01N 63/00
[52] U.S. Cl. .................................... 435/253.3; 424/93.47; 435/877
[58] Field of Search ................................ 435/253.3, 877; 424/934.7

[56] References Cited

U.S. PATENT DOCUMENTS

| | | | |
|---|---|---|---|
| 4,479,936 | 10/1984 | Vandenbergh et al. | 424/93 |
| 4,647,533 | 3/1987 | Weller et al. | 435/29 |
| 4,900,348 | 2/1990 | Hoitnik | 71/6 |

FOREIGN PATENT DOCUMENTS 1316856  4/1993  Canada .

OTHER PUBLICATIONS

Caesar et al., "Growth promotion of apple seedlings and rootstocks by specific strains of bacteria", Phytopathology, 1987, vol. 77, No. 11, pp. 1583–1588.

R.S. Utkhede and T.S.C Li, "Evaluation of *Bacillus subtilis* for Potential Control of Apple Replant Disease," *Journal Phytopathology* 126:305–312 (1989).

R.S. Utkhede and E.M. Smith, "Development of Biological Control of Apple Replant Disease," *Acta Horticulturae* 363:129–134 (1994).

*Primary Examiner*—Sandra E. Saucier
*Assistant Examiner*—Vera Afremova
*Attorney, Agent, or Firm*—M. Howard Silverstein; John D. Fado; Margaret A. Connor

[57] ABSTRACT

A biologically pure culture of *Pseudomonas putida* NRRL B-30041 is described which is highly effective as a biological control agent against replant disease in tree fruits. The invention also encompasses methods of biologically controlling replant disease using the bacterium of the invention, and agricultural compositions which incorporate the strain.

6 Claims, No Drawings

CONTROL OF REPLANT DISEASE OF TREE FRUITS WITH PSEUDOMONAS PUTIDA

BACKGROUND OF THE INVENTION

1. Field of the Invention

The present invention relates to biocontrol of replant disease of tree fruits. More particularly, the invention relates to a unique strain of Pseudomonas putida, methods of using the strain to control replant disease, and agricultural compositions containing the bacterium, which are useful in such methods.

2. Description of the Art

Replant diseases of various crops have been recognized since the late 17th century. In apple, replant disease is widespread and has been documented in all of the major fruit-growing regions of the world. Replant disease of apple is most prominent at sites where replanting occurs after the removal of very old fruit trees, but anecdotal evidence suggests that the disease may also be important in nurseries where previous plantings of apple were grown for one to two years (A. L. Jones and H. S. Aldwinckle, Compendium of Apple and Pear Diseases, APS Press, St. Paul, Minn. (1990)), and development of a soil microflora conducive to the development of replant disease was observed within three years of orchard establishment at a previously uncultivated site in Washington state (M. Mazzola, Phytopathology 87:S63 (1997) (abstract)). Uneven growth of young apple trees is a common indication of apple replant disease, but when severe disease pressure is encountered, poor growth or mortality may be exhibited by a majority of trees in the orchard. Symptoms of apple replant disease include severe stunting, shortened internodes, rosetted leaves, and reduced productivity, and trees possess small root systems with an abundance of fibrous roots, many of which are nonfunctional due to decay (F. L. Caruso et al., Canadian Journal of Botany 67:742–749 (1989); H. Hoestra, Ph.D. Thesis, Meded. Landbouwhogesch, Wageningen (1968); and B. M. Savory, Ph.D. Thesis, University of London, London (1966)).

The primary tree fruit production region in North America resides in the Western United States. Apples are grown on over 200,000 acres in this region and account for 65% of the total U.S. production. In Washington state, apples are grown on approximately 180,000 acres, are the source of nearly 50% of the total United States production, and typically vie with wheat as the major agricultural commodity in the state. In 1996, the Washington apple crop generated over one billion dollars in farm income.

Replant disease is often the major impediment to the establishment of an economically viable orchard on a site previously cropped to apple. In Washington state, failure to control apple replant disease typically will result in a $40,000 per acre reduction in gross returns over a ten year period. In addition to tree replacement costs incurred on sites exhibiting severe replant symptoms, trees affected by the disease begin bearing fruit 2–3 years later than normal and fail to attain yields comparable to those obtained in orchards free of the disease. Apple replant disease is becoming an increasingly important problem as orchard rotations are shortened and availability of land suitable for orchard establishment, but not previously planted to apple, becomes limited. Approximately 10,000 acres of apple are replanted each year in the state of Washington alone, and this figure is continuing to rise. Increased frequency of orchard replacement also has resulted from development of markets for new apple varieties, adoption of intensive orchard practices which utilize compact tree spacing resulting in earlier, higher returns/acre, and adoption of dwarfing rootstocks, which have a shorter economic life expectancy than the seedling rootstocks which they replace (A. B. Peterson, Good Fruit Grower, Wenatchee, Wash. (1992)).

Control of replant problems of tree fruits in the United States has traditionally been achieved through the use of soil fumigants, including methyl bromide. Application costs for pre-plant fumigation using methyl bromide/chloropicrin average $600/acre and associated costs are higher for metam sodium application. However, the parties to the United Nations' Montreal Protocol on Substances that Deplete the Ozone Layer have agreed to a stepped phaseout in the use of methyl bromide prior to elimination of its use by 2010. The United States Congress, by way of the Clean Air Act, has prohibited the production and importation of methyl bromide after Jan. 1, 2001. Other broad spectrum biocides, including metam sodium, telone, and chloropicrin, have been proposed as replacements to methyl bromide; the continued use of each of these materials faces potential obstacles as problems ranging from groundwater contamination to health concerns are raised. For example, while pre-plant application of metam sodium has been utilized by some growers in Washington state, this fumigant has been identified for possible regulatory action under section 210 of the Food Quality Protection Act that amends the Federal Insecticide, Fungicide and Rodenticide Act, and the long-term availability of this material remains in doubt. In addition to potential regulatory restrictions, there are several other disadvantages inherent to the continued use of broad spectrum biocides, including difficulty in application, high cost, and the potential hazards to human health. In addition, at present the expanding organic tree fruit industry has no alternative but preplant fumigation prior to orchard renovation (D. Granatstein, Good Fruit Grower pp. 14–15 (1997)). Orchardists must accept the economic loss associated with the three year period after fumigation in which fruit cannot be marketed as organic. Thus, alternative approaches to the use of preplant soil fumigants in general for control of soilborne diseases are needed to ensure the continued productivity of orchard and fruit tree nursery operations.

Replant disease of apple has been studies by numerous investigators for many years, but the etiology of the disease remains to be clearly defined. Replant disease of apple has been attributed to a variety of biotic and abiotic factors, but the fact that other fruit tree species planted in the same soil grow normally, and that soil pasteurization or fumigation dramatically improve plant growth provide conclusive evidence that this disease is primarily a biological phenomenon rather than the result of abiotic factors. Although soil arsenic residues were implicated as a potential cause of replant disease, Covey et al. (Phytopathology 71:712–715 (1981)) observed no reduction in the growth of apple in soils amended with arsenic at concentrations of up to 200 ppm. Likewise, Merwin et al. (Chemosphere 29:1361–1367 (1994)) found no correlation between arsenic concentration and the growth of apple seedlings in old orchard soils in New York.

Previous studies have suggested that the disease is of complex etiology and the factors implicated as causal agents and predisposing factors have been reported to vary between orchard sites. Numerous soil- and plant-associated microorganisms have been implicated as potential causal agents of apple replant disease. The lesion nematode (Pratylenchus spp.) was thought to have a major role in apple replant disease in the eastern United States (Jaffee et al., Phytopathology 72:247–251 (1982) and Mai et al., Plant Disease 65:859–864 (1981)), British Columbia (Utkhede et al., *Plant and Soil* 139:1–6 (1992)) and Australia (Dullahide et al., *Aust. J. Exp. Agr.* 34:1177–1182 (1994)). However, the data presented in these studies are far from decisive and, in some instances, are in direct conflict with the conclusion that the lesion nematode has a role in this disease phenomenon. For instance, Dullahide et al., supra, concluded that the lesion nematode was an important component of the disease complex in Australia, yet elimination of this nematode had no significant effect on apple growth in any of eight replant soils surveyed, even in soils where pasteurization significantly enhanced apple growth. Utkhede et al., 1992, supra, also concluded that *P. penetrans* contributed to the development of apple replant disease, yet in greenhouse studies there was no correlation between root populations of this nematode and disease severity. In studies conducted by Jaffee et al., *Phytopathology* 72:247–251 (1982), populations of *P. penetrans* did not increase over a six week period of apple seedling growth, and a significant reduction in growth of apple seedlings was only obtained when nematode populations were artificially augmented.

Several studies have suggested a role for soilborne fungi in the etiology of apple replant disease. In certain replant soils, the fungicides captan and mancozeb (MANZATE 200) were as effective as soil pasteurization or fumigation with methyl bromide in controlling apple replant disease (Slykhuis et al., *Can. J. Plant Pathol.* 7:294–301 (1985)). Species of Pythium (Braun, *Can. J. Plant Pathol.* 17:336–341 (1995); Caruso et al., *Can. J. Bot.* 67:742–749 (1989); Jaffee et al., *Plant Disease* 66:942–944 (1982); Sewell, *Ann. Appl. Biol.* 97:31–42 (1981)) and Cylindrocarpon (Braun, supra, and Jaffee et al., *Plant Disease* 66:942–944 (1982)) have repeatedly been implicated as causal agents of apple replant disease. A number of other fungi, including Phytophthora spp., *Armillaria mellea* (Sutton et al., *Plant Disease* 65:330–332 (1981)), *Peniophora sacrata* (Taylor et al., *Can. J. Plant Pathol.* 434:263–265 (1970)), Mortierealla sp., *Torulomyces lagena* and *Trichoderma hamatum* (Utkhede et al., 1992, supra), have been implicated in disease development on a site-specific basis. Other studies have suggested the possible involvement of fluorescent pseudomonads and actinomycetes as potential causal agents of replant disease (Bunt et al., *Meded. Fac. Landbouwwet. Rijksuniv. Gent.* 38:1381–1385 (1973)) and Wescott et al., *Phytopathology* 77:1071–1077 (1987)), however the data implicating these organisms in the disease etiology is tenuous.

Recently, we conducted studies to elucidate the role of different soil microorganisms in the development of apple replant disease at multiple sites in Washington state (Mazzola, *Phytopathology* 87:582–587 (1997); Mazzola, *Phytopathology* 87:S63 (1997) (Abstracts)). The results of these studies demonstrated that fungi are the dominant causal agents of replant disease in Washington state, and that the relative importance of the individual pathogens of species from the genera Cylindrocarpon, Phytophthora, Pythium and Rhizoctonia in disease development varies among sites.

In large part, biological and cultural measures for the control of replant disease have failed to be effective under field conditions and have not been adopted by commercial growers. With the exception of monitoring populations of *P. penetrans*, there is a general absence of studies which have determined the implications of alternative control measures on the populations or activity of putative causal agents of apple replant disease under field conditions.

SUMMARY OF THE INVENTION

The present invention is directed to a biologically pure culture of a bacterium identified as a strain of *Pseudomonas putida*, which strain is highly effective as a biological control agent against replant disease of tree fruit. The subject bacterium is identified as *Pseudomonas putida* isolate 2C8.

The unique strain of the invention has the ability to suppress (inhibit the incidence of or reduce the incidence or severity of) disease in tree fruits caused by one or more of the fungi of the replant disease causal fungal complex, and thereby to control replant disease. Thus, the present invention is also directed to methods of biologically controlling replant disease in tree fruits using the bacterium of the invention.

A still further aspect of the invention pertains to agricultural compositions which incorporate the strain of the invention, and which may be utilized in carrying out the aforementioned methods. Such compositions include the microorganism in combination with an agricultural carrier.

The bacterial biocontrol agent of the present invention may also be used in combination with chemical compounds, including chemical fungicides and nematicides, as discussed below.

In accordance with this discovery, it is an object of the invention to provide a biologically pure culture of a unique strain of *Pseudomonas putida* which is highly effective as a biological control agent against replant disease of tree fruits.

Another object of the invention is the provision of methods for biologically controlling replant disease using the strain of the invention and agricultural compositions which incorporate the strain.

Other objects and advantages of the invention will become readily apparent from the ensuing description.

DETAILED DESCRIPTION OF THE INVENTION

The unique bacterial strain of the invention, designated as *Pseudomonas putida* 2C8, was isolated from the rhizosphere of apple at the Wenatchee Valley College-Auvil Research and Demonstration orchard located approximately 8 km east of East Wenatchee, Wash. This site had not previously been planted to apple prior to orchard establishment and trees at this site were exhibiting excellent growth. It was selected from more than 120 other bacteria and 60 fungi, and was obtained in biologically pure form by dilution plating. The origin and isolation of 2C8 are described in detail, below, in Example 1.

The strain of the invention is highly effective as a biological control agent against replant disease of tree fruits as shown in assays, with apple seedlings, which assess the ability of a microorganism to suppress root colonization by the causal fungal complex of replant disease resulting in enhanced seedling growth and survival. Similar results were obtained in greenhouse trials using seedling rootstocks of a size typically planted by growers in the field. In addition, a field trial with strain 2C8 has demonstrated a similar growth enhancement and suppression of root colonization by elements of the disease complex including *Rhizoctonia solani*.

*Pseudomonas putida* strain 2C8 exhibits inhibitory activity against a broad group of fungi, including Rhizoctonia spp. and Pythium spp. In in vitro agar plate assays (Mazzola et al., *Appl. Environ. Microbiol.* 61:2554–2559 (1995)) the strain exhibited activity against species from each of the major fungal taxonomic groups including ascomycetes, basidiomycetes, zygomycetes and oomycetes. Specific genera evaluated in these assays included, but was not limited to, Alternaria, Cylindrocarpon, Fusarium, Mortierella, Mucor, Phytophthora, Pythium, Ulocladium and Rhizoctonia. All species and anastomosis groups of Rhizoctonia that have been shown to be pathogenic toward apple including *Rhizoctonia solani* AG's 5 and 6, and binucleate Rhizoctonia spp. belonging to AG's G, Q and I.

Strain 2C8 is unique in that it was consistently superior to other fluorescent pseudomonads in suppressing disease development and enhancing the growth of apple in seedling bioassays. This is important because a major limitation to the adoption of biological control agents is the inconsistent performance of these agents when applied under field conditions. In large part, this results from an inability of the introduced agent to persist at the required density in potential infection sites (plant tissue) in competition with the resident microflora. A distinctive attribute of strain 2C8 which, in part, resulted in its selection for further evaluation was its consistent ability to provide control of Rhizoctonia root rot of apple in multiple screening trials conducted in natural soil systems. By definition, natural soil, as opposed to a sterile growth medium, possess an indigenous soil microflora that will compete with any introduced strain to colonize plant roots. This ability also has been demonstrated by the fact that application of strain 2C8 has enhanced the growth of apple and reduced infection by components of the causal fungal complex in field soils from multiple sites exhibiting symptoms of replant disease (see Example 3, below). An additional unexpected attribute of strain 2C8, as its selection was initially selected on the basis of suppression of Rhizoctonia root rot, is its ability to suppress apple root colonization by species of Pythium and Cylindrocarpon (see Example 3, below).

The identifying taxonomic characteristics of *Pseudomonas putida* 2C8 are as follows: Strain 2C8 is a gram negative rod and produces a yellow-brown pigment. It was identified as *Pseudomonas putida* based on carbon utilization analysis with the Biolog system (Biolog, Inc., Hayward, Calif.) which gave a similarity index of 0.841 and by 16S rRNA gene sequence similarity. The portion of DNA analyzed corresponded to *Escherichia coli* positions 005 to 531 of the 16S rRNA gene. Genetic analysis of strain 2C8 using a PCR protocol showed that this strain does not possess phenazine biosynthetic genes.

Carbon utilization test results according to the Biolog system are indicated in parentheses for each carbon source as follows: α-cyclodextrin (−), dextrin (−), glycogen (−), tween 40 (−), tween 80 (+), N-acetyl-D-galactosamine (−), N-acetyl-D-glucosamine (−), adonitol (−), L-arabinose (−), D-arabitol (−), cellobiose (−), I-erythritol (−), D-fructose (−), L-fructose (−), D. galactose (−), gentiobiose (−), α-D-glucose (+), m-inositol (−), α-lactose (−), α-D-lactose lactulose (−), maltose (−), D-mannitol (−), D-mannose (−), D-melibiose (−), β-methyl-D-glucoside (−), psicose (−), D-raffinose (−), L-rhamnose (−), D-sorbitol (−), sucrose (−), D-trehalose (−), turanose (−), xylitol (−), methyl pyruvate (−), mono-methyl succinate (−), acetic acid (+), cis-aconitic acid (+), citric acid (+), formic acid (+), D-galactonic acid lactone (−), D-galacturonic acid (−), D-gluconic acid (+), D-glucosaminic acid (−), D-glucuronic acid (−), α-hydroxy butyric acid (−), γ-hydroxy butyric acid (−), p-hydroxy phenylacetic acid (−), itaconic acid (−), α-keto butyric acid (−), α-keto glutaric acid (+), α-keto valeric acid (−), D, L-lactic acid (+), malonic acid (−), propionic acid (+), quinic acid (+), D-saccharic acid (−), sebacic acid (−), succinic acid (+), bromo succinic acid (+), succinamic acid (−) glucuronamide (−) alaninamide (−), D-alanine (+), L-alanine (+), L-alanyl-glycine (−), L-asparagine (+), L-aspartic acid (+), L-glutamic acid (+), glycyl-L-aspartic acid (−), glycyl-L-glutamic acid (−), L-histidine (+), hydroxy L-proline (−), L-leucine (−), L-ornithine (−), L-phenyl alanine (−), L-proline (+), L-pyro glutamic acid (−), D-serine (−), L-serine (−), L-threonine (−), D, L-carnitine (−), γ-amino butyric acid (−), urocanic acid (−), inosine (−), uridine (−), thymidine (−), phenyl ethylamine (−), putrescine (+), 2-amino ethanol (+), 2,3-butanediol (−), glycerol (+), D, L-α-glycerol phosphate (−), glucose-1-phosphate (−), glucose-6-phosphate (−).

Statement Of Deposit. A biologically pure culture of *Pseudomonas putida* 2C8 was deposited Jul. 10, 1998 under terms of the Budapest Treaty in the Agricultural Research Culture Collection (NRRL), 1815 North University Street, Peoria, Ill. 61604, and has have been assigned the accession number NRRL B-30041. Strains having all the identifying characteristics of NRRL B-30041 are encompassed by this invention. For the purpose of this invention, any isolate having the identifying characteristics of strain 2C8, including subcultures and variants thereof which retain the ability to control replant disease in tree fruits, are included. The term variants is defined herein to include transformants and mutants which are capable of controlling replant disease of tree fruits.

Growth of the strain of the invention. *Pseudomonas putida* strain 2C8 can be grown on any suitable solid or liquid bacteriological medium. For routine production of strain 2C8 for treatment of replant disease in the laboratory or the field, the bacterium is grown in nutrient-yeast extract (NBY) broth (3 g bacto beef extract, 5 g bacto peptone, 2 g yeast extract, 5 g glucose in 1 L deionized water) for 18 h at 28° C. Cells are collected by centrifugation (12000 rpm for 10 min). Cells are washed once in sterile deionized water, collected by centrifugation, and resuspended in 10 mM potassium phosphate buffer (pH 7.0). Cell concentration is adjusted using spectrophotometry; an absorbance of 0.1 at 600 nm wavelength indicates a concentration of approximately $10^7$ cfu/ml. Strain 2C8 is conveniently stored on silica gel at −20° C. To do this, it is transferred with a loop from a 24-hour culture on NBY agar to 4.8% milk. Conveniently, a 100 μl aliquot of the suspension is pipetted onto 1.5 g of silica gel in a 6-ml vial. New cultures are periodically started by sprinkling silica gel onto NBY agar media.

Use of the strain of the invention. *Pseudomonas putida* 2C8 is useful in the control of replant disease of tree fruits. The term tree fruits applies to plants in the family Rosaceae. For purposes of this invention, control means that the frequency of disease, e.g., root infection, by individual fungi of the causal fungal complex (for example, Rhizoctonia spp. and/or Pythium spp.) is reduced relative to the nontreated trees. Consequently the incidence or severity of replant disease is reduced or prevented. The affect of control treatments on disease will be evidenced by one or more of the following: an increase in trunk cross-sectional area, increased shoot elongation, and increases in root and shoot weights compared to nontreated plants. In a commercial setting, control of replant disease may be viewed by the grower as increased vegetative growth.

The strains are preferably incorporated into compositions suitable for application to tree fruit trees, preferably for root application. It can be mixed with any agriculturally acceptable carrier or suitable agronomically acceptable carrier which does not interfere with the activity of the strain, for example, water or buffer. Where the strain is applied as a suspension or emulsion in a liquid carrier, the suspension or emulsion may optionally contain conventional additives such as surfactants, wetting agents, sticking agents, e.g., methylcellulose, or chemical inhibitors as known in the art.

The strain of the invention can also be formulated to include other strains which control other tree fruit diseases, or formulated in conjunction with a fungicide or nematicide as discussed below.

Application procedures and parameters. The organism of the invention is applied as a root-dip, as a soil drench, incorporated into soil on an appropriate solid-based carrier (compost) or through a combination of these methods. The organism should be applied at planting, with additional applications made as a soil drench should disease severity warrant. Treated ground should be watered immediately after application of the organism to facilitate movement into the root zone and to enhance survival of the organism.

The strain is applied in an effective amount. For the purposes of this invention, an effective amount is defined as that quantity of microorganism cells sufficient to inhibit the incidence or development of replant disease. Typically a concentration range from about $1 \times 10^6$ to $3 \times 10^8$ colony forming units (cfu)/ml is effective when applied as a root-dip to planting stock trees. The preferred concentration range for root-dip application is about $1 \times 10^7$ to $1 \times 10^8$ cfu/ml; however, concentrations as low as $1 \times 10^6$ cfu/ml may be useful in some cases when applied as a root-dip. Generally, a concentration range of about $1 \times 10^5$ to $1 \times 10^8$ cfu/ml is effective when the bacterium is applied as a soil drench. The preferred concentration for soil drench application is about $1 \times 10^7$ to $1 \times 10^8$ cfu/ml, with about 6–8 L applied to each tree.

The effective rate can be affected by environmental factors, particularly inoculum potential at a site, which can affect both the biocontrol agent and the pathogen. Disease pressure can vary significantly between orchards and can be affected by the composition of the resident microbial community, the population genetics of the pathogen, attributes of the host, and other environmental parameters. Thus, the application rate necessary to achieve effective disease control can be reduced where inoculum potential of the pathogen complex is lower, but may require higher rates or repeated applications where inoculum potential of the pathogen complex is high. The amount that will be within an effective range in a particular instance can be determined by laboratory assays.

Application of this agent as a stand alone treatment is not recommended on sites possessing significant populations of the lesion nematode, Pratylenchus spp., but can be efficacious in such environments when applied in conjunction with nematicides that are compatible with the bacterial strain, for example, ethyl 3-methyl-4-(methylthio) phenyl (1-methylethyl) phosphoramidate (NEMACUR).

Although *P. putida* strain 2C8 demonstrated the ability to suppress in vitro mycelial growth of *Phytophthora cactorum*, when applied as a root-dip this bacterium did not appear to suppress the incidence of apple root infection by *Phytophthora cactorum* in orchard replant soils. As *P. cactorum* commonly is a component of the causal biological complex inciting apple replant disease, application of strain 2C8 will commonly be carried out in conjunction with a fungicide effective against Phytophthora, for example, soil drench application of the fungicide nietalaxyl (RIDOMIL) or foliar application of the fungicide aluminum tris (O-ethyl phosphonate) [ALIETTE].

EXAMPLES

The following examples are intended only to further illustrate the invention and are not intended to limit the scope of the invention which is defined by the claims.

Example 1

The following example describes the origin and isolation of *Pseudomonas putida* strain 2C8.

*Pseudomonas putida* strain 2C8 was recovered from the rhizosphere of apple at the Wenatchee Valley College-Auvil Research and Demonstration Orchard located approximately 8 km east of East Wenatchee, Wash. This isolate was part of a microbial collection which was evaluated for its ability to suppress *Rhizoctonia solani* AG 5, a pathogen that is a component of the fungal complex which incites apple replant disease, but is also capable of causing root rot of apple. The organism was isolated from the rhizosphere of a two-year-old tree of the cultivar 'Fuji' on M.26 rootstock. Roots and firmly adhering soil from this tree were placed in 10 ml sterile water and vortexed for 60 sec. Serial dilutions of this root wash were plated onto $\frac{1}{10}$th strength tryptic soy agar. Resulting individual colonies were transferred to NBY agar, and the resulting bacterial growth was streaked for single cells onto a fresh plate of NBY agar. An individual colony from this plate was streaked onto a fresh plate of NBY agar to ensure that the culture was biologically pure. Growth from this culture was used in preparation for storage on silica gel as described above.

Stock cultures are maintained and stored as a 45% glycerol/NBY broth suspension. Stock cultures were prepared by growing the organism on NBY agar, and transferring the 24 hr growth using a sterile loop to the glycerol/NBY broth solution. Cultures were stored in 2 ml cryovials at −20° C.

Example 2

This example describes the selection of strain 2C8 from among other microorganisms.

The strain 2C8 was selected from more than 120 other bacteria and 60 fungi that have been tested to date in the laboratory for potential use in the biological control of replant disease. Bacteria were screened in assays which were conducted in controlled environment chambers and the greenhouse. In initial trials, organisms were screened for the ability to suppress growth of *Rhizoctonia solani* AG 5. In subsequent trials, these organisms were screened for the ability to enhance the growth of apple in soils collected from orchards that were exhibiting symptoms of replant disease. Strains which demonstrated the ability to enhance growth of apple in these replant soils were then evaluated for their ability to suppress colonization of apple roots by components of the fungal complex which incites replant disease.

For screening trials, bacterial inoculum was prepared by culturing in NBY broth with aeration (200 rpm on a Lab Line orbit enviro shaker) for 18 h at 28° C. Cells were collected by centrifugation at 12,000 rpm for 10 min, washed once in sterile distilled water, and resuspended in 10 mM potassium phosphate buffer (pH 7.0). Suspensions were adjusted to a concentration of approximately $10^6$ cfu/ml in 0.5% methylcellulose. Bacteria were applied to 5-week-old apple seedlings (cultivar 'Gala') by suspending the plant root system in the bacterial suspension for 30 sec. Treated seedlings were cultivated in apple replant soils, and shoot and root weights were determined after 4 weeks of growth.

Among the more than 120 bacteria and 60 fungi tested, strain. 2C8 was the most effective and consistent in suppressing replant disease and enhancing growth of apple.

Example 3

This example describes assays to determine the effect of *Pseudomonas putida* 2C8 root-dip application on the growth of apple seedlings or rootstock in orchard replant soil.

Initial trials were conducted in soil from the DR orchard located near Moxee, Wash. Assays were conducted in controlled environment chambers using 'Gala' apple seedlings as the planting stock. Strain 2C8 was grown overnight in nutrient broth yeast extract medium and cells were pelleted and washed twice prior to resuspension of the cells in 0.5% methyl cellulose solution. The cell suspension was adjusted to $10^6$ cfu/ml prior to plant treatment. Seedling roots were dipped into the cell suspension for 30 sec. Plants were grown in cone-tainer growth tubes at a constant temperature of 18° C. with a 12 h photoperiod. Plants were harvested after 4 weeks and plant dry-weights were determined.

As can be seen from Table 1, below, *P. putida* consistently enhanced the growth of apple seedlings in the DR replant soil. The 2C8 treatments were significantly different from the control at P=0.05 based on Fisher's least significant difference test.

Table 1. Effect of *Pseudomonas putida* 2C8 root-dip application on growth of 'Gala' apple seedlings in DR orchard replant soil.

TABLE 1

Effect of *Pseudomonas putida* 2C8 root-dip application on growth of 'Gala' apple seedlings in DR orchard replant soil.

| Treatment | Exp. 1 Plant weight (mg) | Exp. 2 Plant weight (mg) |
| --- | --- | --- |
| Control | 681 | 489 |
| P. putida 2C8 | 813 | 670 |

Additional trials with strain 2C8 were conducted WVC-SS orchard soil (from Wenatchee, Wash.) and GC orchard soil (from near Manson, Wash.), using one-year-old seedling rootstocks as the planting material. A suspension of strain 2C8 ($10^7$ cfu/ml) in 0.5% methylcellulose was prepared and rootstocks were dipped for a period of 30 sec prior to planting. Trees were grown for 10–12 weeks when root weight and/or shoot elongation was assessed for each tree.

Table 2. Effect of *Pseudomonas putida* 2C8 root-dip application on growth 'Seedling' rootstock in WVC-SS and GC orchard replant soils.

TABLE 2

Effect of *Pseudomonas putida* 2C8 root-dip application on growth 'Seedling' rootstock in WVC-SS and GC orchard replant soils.

| Treatment | WVC-SS orchard Shoot length (cm) | Root wt. (g) | GC orchard Shoot length (cm) |
| --- | --- | --- | --- |
| Control | 4.6 | 21.8 | 22.9 |
| P. putida 2C8 | 14.5 | 31.9 | 31.8 |

Strain 2C8 significantly improved the growth of apple trees in both WVC-SS and GC orchard soils (P=0.05 based on Fisher's least significant difference test). This finding is of importance due to the relative differences in the fungal complex responsible for disease development at these sites. Analysis of the fungal community colonizing apple trees planted in WVC-SS soil provided evidence that strain 2C8 enhanced plant growth via the suppression of *Rhizoctonia solani* and Pythium spp. *Pythium ultimum* and *P. sylvaticum* comprised 17.8% of the fungal population recovered from nontreated trees but only 5.2% of the isolates recovered from trees treated with strain 2C8. Isolation of *Rhizoctonia solani* and *Cylindrocarpon destructans* declined from 6.3% to 0.6% and 34% to 23%, respectively, of the total fungal population recovered from apple trees in response to root application of strain 2C8. Frequency of isolation of *Pytophthora cactorum* from apple roots was not diminished by application of this rhizobacterium.

In a preliminary field trial conducted in May 1997 at the WVC-SS orchard, strain 2C8 was applied to apple trees ('Gala' on M.26 rootstock) as a root-dip. Strain 2C8 was suspended in 0.5% methylcellulose at a concentration of $10^7$ cfu/ml. Increase in shoot length and cross-sectional area was determined at the end of the growing season in October 1997. Strain 2C8 significantly (P=0.05 based on Fisher's least significant difference test) enhanced tree cross-sectional area but no significant increase in tree shoot length was observed (Table 3).

Table 3. Effect of *Pseudomonas putida* strain 2C8 root-dip application on growth of 'Gala' on M.26 root stock at the WVC-sunnyslope orchard in Wenatchee, Wash.

TABLE 3

Effect of *Pseudomonas putida* strain 2C8 root-dip application on growth of 'Gala' on M.26 root stock at the puz,4/29 WVC-sunnyslope orchard in Wenatchee, WA.

| Treatment | Increase in tree diameter (mm) | Shoot length (cm) |
| --- | --- | --- |
| Control | 2.32 | 23.5 |
| P. putida 2C8 | 3.20 | 25.6 |

On May 5, 1998, a field trial to assess the efficacy of *Pseudomonas putida* strain 2C8 was established at the Washington State University/USDA-ARS Columbia View orchard located near East Wenatchee, Wash. Strain 2C8 was prepared by growing overnight in NBY broth, cells were washed, and resuspended in a 0.5% methylcellulose solution to obtain a final concentration of $1\times10^8$ cells per ml. Apple trees ('Gala' on M.26 rootstock) were dipped into the bacterial suspension for 1.5 minutes and planted. Immediately after planting, 1.5 L of the bacterial suspension was applied to the soil surface and washed into the soil profile by the application of 10 L of water. Plant shoot lengths were measured on Jun. 27 and Jul. 13, 1998. Soil fumigation and application of strain 2C8 resulted in a significant (P=0.0033) increase in shoot length relative to the control (Table 4).

TABLE 4

Effect of *Pseudomonas putida* strain 2C8 on growth of 'Gala' on M.26 root stock at the CV orchard near E. Wenatchee, WA

| | Shoot Length (cm) | |
| --- | --- | --- |
| Treatment | 27 June | 13 July |
| Control | 22.6a | 24.2a |
| Fumigation | 26.9b | 30.4b |
| P. putida 2C8 | 27.2b | 30.7b |

Values in the same column followed by the same letter are not significantly (P = 0.01) different based on Fusher's least significant difference test.

It is understood that the foregoing detailed description is given merely by way of illustration and that modification and variations may be made within, without departing from the spirit and scope of the invention.

What is claimed is:

1. A biologically pure culture of a strain of *Pseudomonas putida* having all of the identifying characteristics of *Pseudomonas putida* NRRL B-30041.

2. A composition for controlling replant disease on tree fruits, which comprises the strain of claim 1 and an agriculturally acceptable carrier.

3. The composition as described in claim 2 wherein said carrier comprises water.

4. The composition as described in claim 2 wherein said strain is present in an amount effective to inhibit the incidence or severity of replant disease on tree fruits.

5. A method of inhibiting the incidence or severity of replant disease on tree fruits, which comprises applying to roots or root zone of a tree of the Rosaceae, an effective inhibiting amount of the biologically pure culture of claim 1.

6. A method of controlling replant disease on tree fruits, which comprises applying an effective replant disease-inhibiting amount of the biologically pure culture of claim 1 by root-dip application, by soil drench application, by application into soil on a solid-based carrier or by a combination of said applications.

* * * * *